United States Patent
Nakaji et al.

(10) Patent No.: US 10,041,990 B2
(45) Date of Patent: Aug. 7, 2018

(54) WATER TREE TESTING METHOD AND WATER TREE TESTING APPARATUS

(71) Applicant: TOSHIBA MITSUBISHI-ELECTRIC INDUSTRIAL SYSTEMS CORPORATION, Chuo-ku (JP)

(72) Inventors: Hirotake Nakaji, Tokyo (JP); Yuichi Tsuboi, Tokyo (JP); Toshihiro Tsuda, Tokyo (JP); Tetsuo Yoshimitsu, Tokyo (JP)

(73) Assignee: TOSHIBA MITSUBISHI-ELECTRIC INDUSTRIAL SYSTEMS CORPORATION, Chuo-ku (JP)

( * ) Notice: Subject to any disclaimer, the term of this patent is extended or adjusted under 35 U.S.C. 154(b) by 0 days.

(21) Appl. No.: 15/532,684

(22) PCT Filed: Dec. 5, 2014

(86) PCT No.: PCT/JP2014/006100
§ 371 (c)(1),
(2) Date: Jun. 2, 2017

(87) PCT Pub. No.: WO2016/088156
PCT Pub. Date: Jun. 9, 2016

(65) Prior Publication Data
US 2017/0336466 A1 Nov. 23, 2017

(51) Int. Cl.
*G01R 31/20* (2006.01)
*G01R 31/12* (2006.01)
*G01N 17/00* (2006.01)

(52) U.S. Cl.
CPC ............ *G01R 31/20* (2013.01); *G01N 17/00* (2013.01); *G01R 31/1272* (2013.01)

(58) Field of Classification Search
CPC .. G01R 31/003; G01R 31/12; G01R 31/1227; G01R 31/1263; G01R 31/1272;
(Continued)

(56) References Cited

U.S. PATENT DOCUMENTS 4,144,202 A * 3/1979 Ashcraft .............. C08K 5/5435
174/110 PM
4,305,849 A 12/1981 Kawasaki et al.
(Continued)

FOREIGN PATENT DOCUMENTS

JP 56-028231 A 3/1981
JP 57-126004 A 8/1982
(Continued)

OTHER PUBLICATIONS

International Search Report dated Feb. 10, 2015 in PCT/JP2014/006100, filed Dec. 5, 2014.

*Primary Examiner* — Tung X Nguyen
*Assistant Examiner* — David Frederiksen
(74) *Attorney, Agent, or Firm* — Oblon, McClelland, Maier & Neustadt, L.L.P.

(57) ABSTRACT

A water tree testing apparatus using a flat test piece comprising a candidate insulation material an d having a first surface having a plurality of electrode holes formed therein has: a liquid-permeable conductive first permeable member that is attached to the first surface and covers the electrode holes; a liquid-permeable conductive second permeable member that is attached to a second surface that is opposite side from the first surface, and extends along the second surface as to face the first permeable member with the test piece therebetween; a first water tank for immersing the first surface in the first aqueous solution; a second water tank for immersing the second surface in the second aqueous solution; a first electrode, and a second electrode.

4 Claims, 5 Drawing Sheets

(58) Field of Classification Search
CPC ........ G01R 31/14; G01R 31/16; G01R 31/20; G01N 17/00; H02K 3/44
See application file for complete search history.

(56) References Cited

U.S. PATENT DOCUMENTS

| | | | |
|---|---|---|---|
| 4,535,116 A | | 8/1985 | Johnson et al. |
| 4,612,139 A | | 9/1986 | Kawasaki et al. |
| 5,276,401 A | * | 1/1994 | Soma .................. G01R 31/021 324/544 |
| 6,340,891 B1 | * | 1/2002 | Yagi .................... G01R 31/021 324/544 |
| 2012/0306510 A1 | * | 12/2012 | White .................. G01R 31/021 324/551 |
| 2016/0161541 A1 | * | 6/2016 | Kim .................... G01R 31/021 702/58 |

FOREIGN PATENT DOCUMENTS

| | | |
|---|---|---|
| JP | 04-311742 A | 11/1992 |
| JP | 11-350918 A | 12/1999 |
| JP | 2012-103158 A | 5/2012 |

* cited by examiner

WATER TREE TESTING METHOD AND WATER TREE TESTING APPARATUS

TECHNICAL FIELD

The present invention relates to a water tree testing method and a water tree testing apparatus.

BACKGROUND ART

Some cables that can be laid underwater have copper wires, or conductors, covered with an insulator made of polymeric material and the like. For example, thermosetting resins, such as cross-linked polyethylene (hereinafter, referred to as XLPE.), and thermoplastic resins are often used as the polymeric material.

Some insulated cables laid underwater are used to transmit alternating-current voltage, an inverter voltage (repetitive impulse bipolar voltage), and the like. Such insulated cables can cause a water tree in XLPE and other insulators if used for several years under an alternating repetitive impulse bipolar voltage including inverter surges. A water tree refers to a branch-like insulation degradation phenomenon which occurs in the insulation material of the insulator if an electric field acts on the insulator for a long time in the presence of water. The water tree eventually induces an electrical breakdown.

As a water tree diagnosis technique, an insulation diagnostic system and the like for making an insulation diagnosis of lightening arresters and power cables with a power system stopped have been known (see Patent Literature 1).

The status of occurrence and the like of a water tree need to be figured out in advance in order to select materials for use in the insulators of insulated cables laid underwater and to design their structure. For that purpose, a test for generating, i.e., reproducing a water tree needs to be performed.

Figure 5:
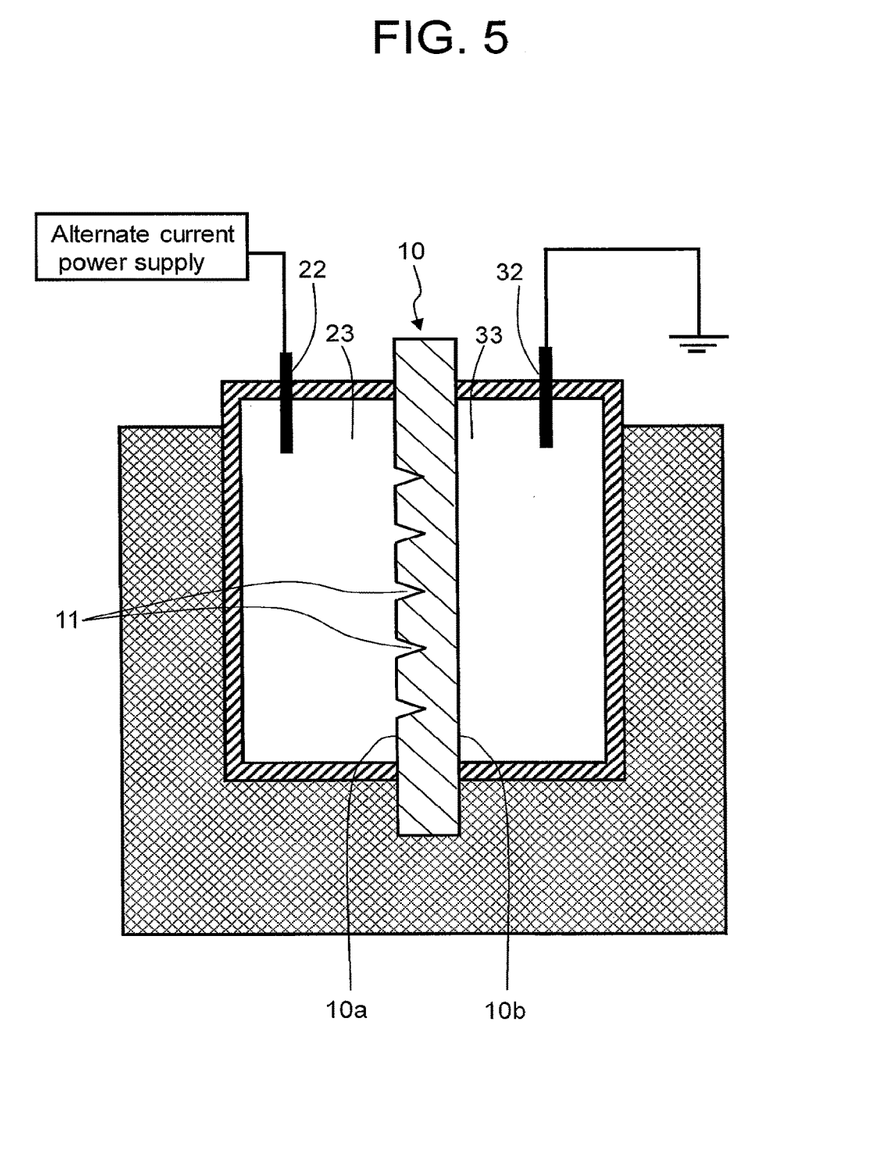
FIG. 5 is a sectional elevational view showing a configuration of a conventional water tree testing apparatus.

Such methods as a water electrode method are used to generate a water tree. FIG. 5 is a sectional elevational view showing a configuration of a conventional water tree testing apparatus. This water electrode method uses a flat test piece 10 of XLPE in which many electrode holes (recesses) 11 are formed. A surface, where the electrode holes 11 are formed, of the test piece is immersed in an application-side aqueous solution 23. The other surface is immersed in a ground-side aqueous solution 33. In such a state, a relatively high electric field is generated near each of the electrode holes 11. A water tree can thus be reproduced in the XLPE around each electrode hole 11.

PRIOR ART DOCUMENT

Patent Document

Patent Document 1: Japanese Patent Application Laid-Open Publication No. HEI 11-350918

SUMMARY OF THE INVENTION

Problems to be Solved by the Invention

In the water electrode method, the test piece 10 is immersed in the solutions as described above. A relatively high electric field is generated near the electrode holes 11 of the test piece 10. In order to realize those states, an application-side electrode 22 is inserted into the application-side aqueous solution 23 and a ground-side electrode 32 is inserted into the ground-side aqueous solution 33, with the test piece 10 therebetween. A voltage is applied in a configuration that: the application-side electrode 22 provided in the application-side aqueous solution 23 on the first surface 10a side of the test piece 10, where the electrode holes 11 are formed, corresponds to a high voltage side; and the ground-side electrode 32 provided in the ground-side aqueous solution 33 on the other, second surface 10b side corresponds to a low voltage side. To examine a voltage polarity effect and the like, a unipolar voltage may be applied in the following configuration. That is, the application-side electrode 22 provided in the application-side aqueous solution 23 on the first surface 10a side of the test piece 10, where the electrode holes 11 are formed, is a positive side. And the ground-side electrode 32 provided in the ground-side aqueous solution 33 on the other, second surface 10b side is a negative side, or vice versa.

The electrode holes 11 are arranged in parallel to each other spreading in a plane, at a plurality of locations vertically and horizontally. The electrical field formed by the application of the voltage is thus desirably uniformly extended along the plane.

The electrodes 22 and 32 are typically bar electrodes. The electric field formed by the two electrodes 22 and 32 is therefore not uniform with respect to the electrode holes 11 of the test piece 10. If the test piece 10 is tested by such a method, the electrode holes 11 are not in a uniform electric field, and pieces of data cannot be regarded as those obtained in an equal environment.

The present invention has been achieved in view of the foregoing, and the object thereof is to improve test accuracy by applying a uniform electric field to a plurality of electrode holes during a water tree reproducing test.

Means for Solving the Problem

According to the present invention, there is provided a water tree testing apparatus to reproduce a water tree phenomenon for a water tree resistance evaluation of a candidate insulation material by using a flat test piece of the candidate material, the test piece having a first surface in which a plurality of electrode holes are formed, the electrode holes being formed to decrease in cross section as approaching a bottom perpendicularly to the surface, the water tree testing apparatus comprising: a liquid-permeable conductive first permeable member that is adhered to the first surface and extends along the first surface to cover the electrode holes; a liquid-permeable conductive second permeable member that is adhered to a second surface that is opposite side from the first surface, and extends along the second surface as to face the first permeable member with the test piece therebetween; a first water tank that contains a first aqueous solution so that the first surface of the test piece including a range covered by the first permeable member is immersed in the first aqueous solution; a second water tank that contains a second aqueous solution so that the second surface of the test piece including a range covered by the second permeable member is immersed in the second aqueous solution; a first electrode whose one end is electrically connected to the first permeable member; and a second electrode whose one end is electrically connected to the second permeable member, wherein the first electrode and the second electrode are formed so that a voltage is applicable therebetween.

According to the present invention, there is provided a water tree testing method for replicating a water tree phenomenon for a water tree resistance evaluation of a candidate insulation material by using a test piece of the insulation material, the water tree testing method comprising: a system setting step of setting a test system in such a state that a first permeable member is adhered to a first surface of the test piece and the first surface is immersed in a first aqueous solution, and a second permeable member is adhered to a second surface on a back side of the first surface and the second surface is immersed in a second aqueous solution, wherein the test piece is made of the candidate material, has a flat shape, and has a plurality of electrode holes formed in the first surface, and the electrode holes are formed to decrease in cross section as approaching a bottom perpendicularly to the surface; a voltage application step of grounding either the first electrode immersed in the first aqueous solution or the second electrode immersed in the second aqueous solution and applying an alternating-current voltage to the other after the system setting step;

a measurement step of measuring an amount of development of a water tree in the test piece at predetermined time intervals after a start of the voltage application step; and a repeat step of determining whether a predetermined time of test time has elapsed after the measurement step, and if the predetermined time has elapsed, terminating the measurement step, and if the predetermined time has not elapsed, repeating the voltage application step and the measurement step.

Advantage of the Invention

According to the present invention, test accuracy can be improved by applying a uniform electric field to a plurality of electrode holes during a water tree reproducing test.

EMBODIMENTS FOR CARRYING OUT THE INVENTION

An embodiment of a water tree testing method and a water tree testing apparatus according to the present invention will be described below with reference to the drawings.

Figure 1:
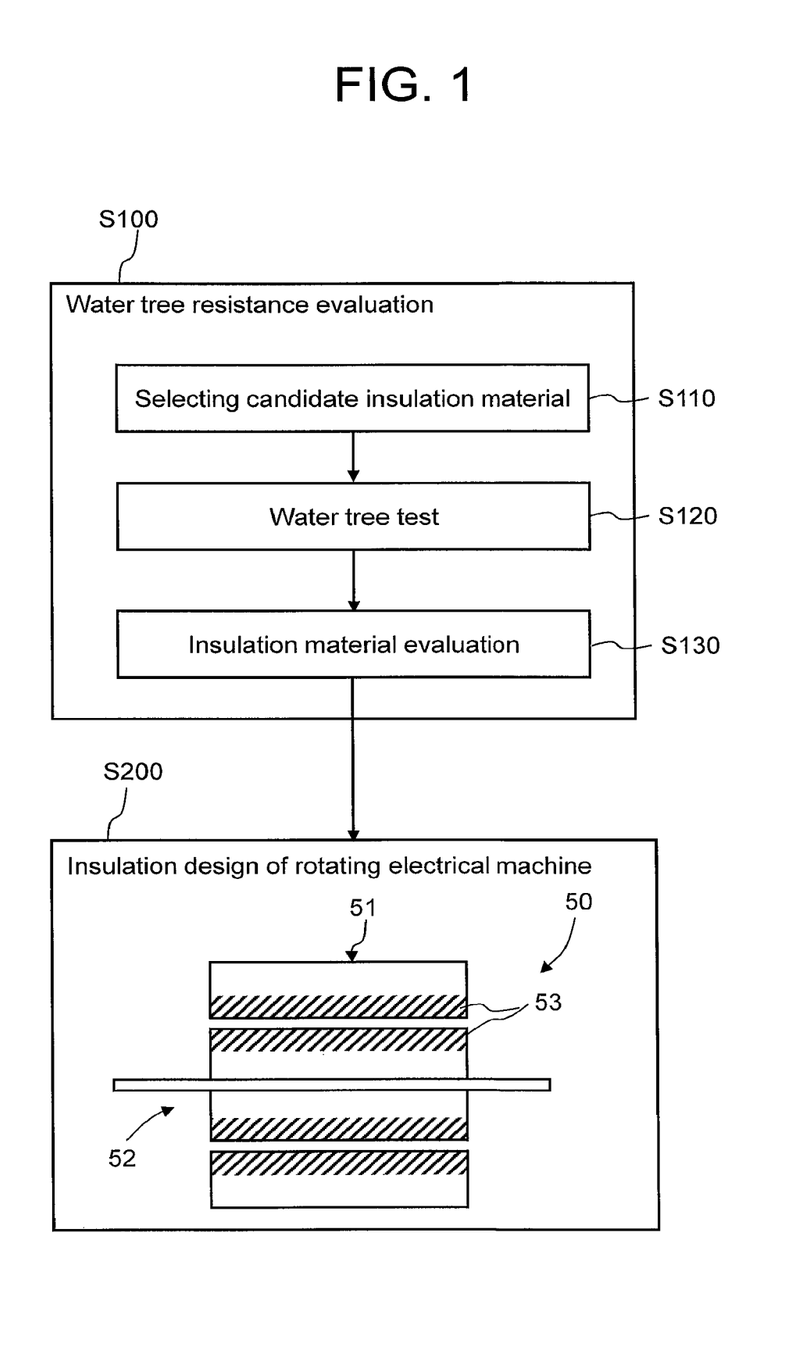
FIG. 1 is a flowchart showing a procedure related to a water tree testing method according to a present embodiment.

FIG. 1 is a flowchart showing a procedure related to a water tree testing method according to a present embodiment. In other words, FIG. 1 shows a procedure of an entire insulation design method including a water tree test. The insulation design method includes a water tree resistance evaluation step S100 and an insulation design step S200 of the rotating electrical machine. The water tree resistance evaluation step S100 is that of evaluating water tree resistance of insulation material used in an insulation member 53 intended to insulate coils and the like of a stator 51 and a rotor 52 of a rotating electrical machine 50. The insulation design step S200 is that of performing an insulation design of the rotating electrical machine.

The water tree resistance evaluation step S100 includes a step (step S110) of selecting a candidate insulation material to be a candidate, a water tree testing step (step S120) of performing a water tree test on the selected candidate insulation material, and an insulation material evaluation step (step S130) of evaluating an insulation performance characteristic of the insulation material tested as the candidate on the basis of the test result.

Figure 2:
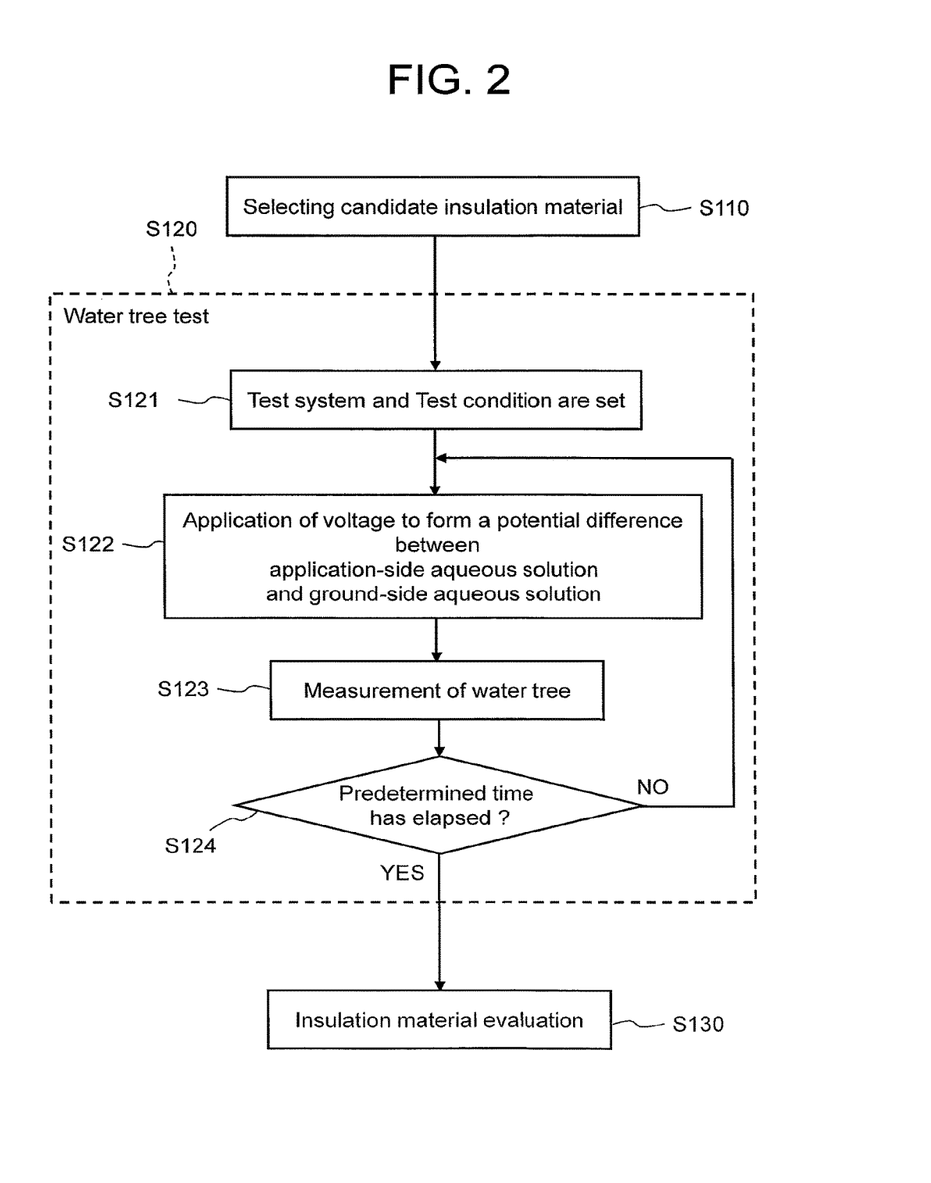
FIG. 2 is a flowchart showing a procedure of the water tree testing method according to the present embodiment.

FIG. 2 is a flowchart showing a procedure of the water tree testing method according to the present embodiment. In step S120 of the water tree test, a test system and a test condition are initially set (step S121). Details of the test system and the test condition will be described referring to FIG. 3.

After step S121, an alternating-current power supply 40 (see FIG. 3) applies a voltage to form a potential difference between an application-side aqueous solution 23 (see FIG. 3) and a ground-side aqueous solution 33 (see FIG. 3), whereby a voltage is applied to a test piece 10 (see FIG. 3) (step S122).

After step S122, the amounts of development of water trees are measured at time intervals (step S123). In addition, whether a predetermined time, i.e., a desired test time has elapsed is determined (step S124). If a predetermined time has not elapsed (step S124, NO), step S122 and the subsequent steps are repeated. If a predetermined time has elapsed (step S124, YES), the test ends.

Figure 3:
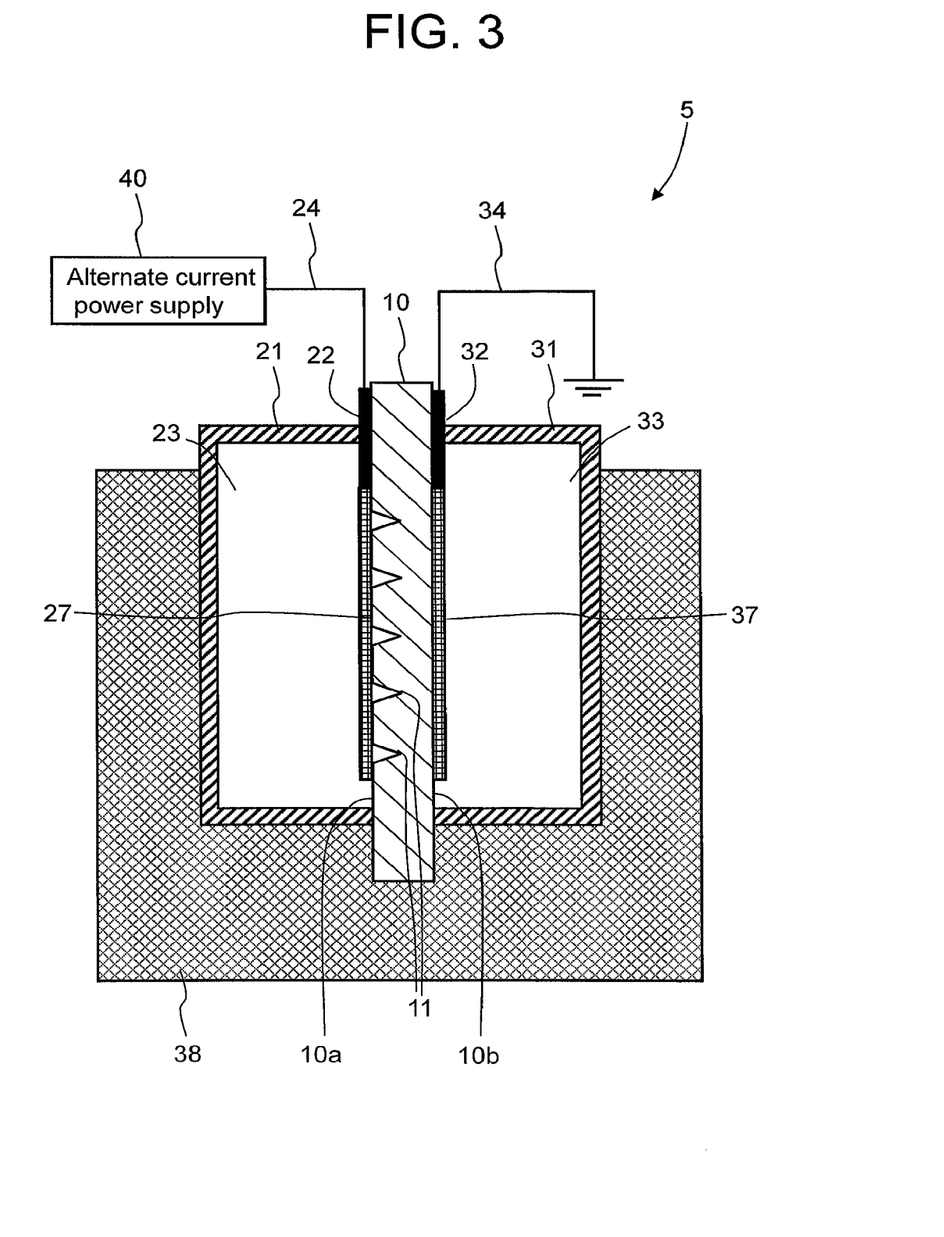
FIG. 3 is a sectional elevational view showing a configuration of a water tree testing apparatus of the present embodiment.

FIG. 3 is a sectional elevational view showing a configuration of the water tree testing apparatus according to the present embodiment. A testing apparatus 5 performs a test by using the test piece 10, and includes an application-side water tank 21, an application-side electrode 22, a ground-side water tank 31, and a ground-side electrode 32. The application-side electrode 22 is connected to the alternating-current power supply 40 by a conductive wire 24. The ground-side electrode 32 and a grounding point are connected by a conductive wire 34. The application-side water tank 21 and the ground-side water tank 31 are containers made of metal. However, the containers are not limited to metal ones. For example, polyethylene and other polymer compound containers can be used.

The test piece 10 is made of an insulation material such as cross-linked polyethylene (XLPE). The test piece 10 has a thick rectangular flat-plate shape, and includes a first surface 10a of wider surfaces and a second surface 10b that is reverse side of the first surface. The first surface 10a and the second surface 10b are both formed to be flat and to be parallel to each other. The first surface 10a has a plurality of electrode holes 11 formed perpendicularly to the surface. Each of the electrode holes 11 is formed to have a conical tip so as to decrease in cross section as approaching the bottom. The electrode holes 11 are so formed as that the distance between the bottoms of the electrode holes 11 and the second surface 10b have a predetermined distances. The number of electrode holes 11 may be set according to such factors as statistical reliability of the test result, or the frequency of status checks of the test piece 10 during the test time.

The electrode holes 11 may be formed, for example, by pressing a member having pointed protrusions into the surface of a warmed insulation material, cooling the same, and pulling out the member. If the characteristic of the insulation material around the electrode holes 11 can be affected by such a method, the electrode holes 11 may be manufactured by a method of pouring an insulation material into a mold for molding. Here, a mold having protrusions corresponding to the shapes of the voids of the electrode holes 11 on its bottom can be used to accurately form the shapes of the electrode holes 11. The electrode holes 11 can be formed without affecting the characteristic of the insulation material around the electrode holes 11.

In the testing apparatus 5 according to the present embodiment, an electrically conductive, liquid-permeable application-side permeable member 27 is attached to part of the first surface 10a to cover all of the electrode holes 11 and extend along the first surface 10a. The application-side permeable member 27 is electrically connected to the application-side electrode 22.

An electrically conductive, liquid-permeable ground-side permeable member 37 is attached to the second surface 10b and extends along the second surface 10b as to face the application-side permeable member 27 with the test piece 10 therebetween. The ground-side permeable member 37 is electrically connected to the ground-side electrode 32.

For example, the application-side permeable member 27 and the ground-side permeable member 37 may be porous metals. In such a case, ones having hole diameters of, e.g., approximately 500 μm and a porosity of 90% or above may be used. The application-side permeable member 27 and the ground-side permeable member 37 are not limited to porous metals. Conductive metal meshes may be used as long as the meshes are electrically conductive and permeable to liquid.

In the testing apparatus 5, the application-side water tank 21 and the ground-side water tank 31 are containers open to one side. The application-side water tank 21 and the ground-side water tank 31 are configured to sandwich the test piece 10 therebetween.

It is necessary to ensure sealability of both the contact portion between the open end of the application-side water tank 21 and the first surface 10a and the contact portion between the open end of the ground-side water tank 31 and the second surface 10b. For example, the open end of the application-side water tank 21 and the first surface 10a, and the open end of the ground-side water tank 31 and the second surface 10b, may be pressed against each other with their rim portions made of elastic material or with an O ring interposed therebetween. Alternatively, the gap between the open end of the application-side water tank 21 and the first surface 10a and the gap between the open end of the ground-side water tank 31 and the second surface 10b may be sealed by respective sealing members or the like.

The test piece 10, the application-side water tank 21, and the ground-side water tank 31 are mostly surrounded by an insulator 38 except their tops. This can prevent the testing apparatus 5 from electrical contact with the outside.

The application-side aqueous solution 23 is encapsulated in the application-side water tank 21. The ground-side aqueous solution 33 is encapsulated in the ground-side water tank 31. For example, the application-side aqueous solution 23 and the ground-side aqueous solution 33 may be a neutral aqueous solution such as sodium chloride aqueous solution. The application-side aqueous solution 23 and the ground-side aqueous solution 33 may have the same concentration. Water may be used as the application-side aqueous solution 23 and the ground-side aqueous solution 33.

The application-side electrode 22 extends through a top wall of the application-side water tank 21. One end of the application-side electrode 22 lies outside the application-side water tank 21, and the other end is immersed in the application-side aqueous solution 23 in the application-side water tank 21. The end of the application-side electrode 22 outside the application-side water tank 21 is connected to the alternating-current power supply 40 via the conductive wire 24.

The ground-side electrode 32 is attached to the ground-side water tank 31. The ground-side electrode 32 extends through a top wall of the ground-side water tank 31. One end of the ground-side electrode 32 lies outside the ground-side water tank 31, and the other end is immersed in the ground-side aqueous solution 33 in the ground-side water tank 31. The end of the ground-side electrode 32 outside the ground-side water tank 31 is connected to the grounded portion via the conductive wire 34.

The applied voltage here is a voltage to which the rotating electrical machine 50 is subjected during operation or a voltage having a value obtained by multiplying the voltage by a predetermined safety factor. In particular, insulation and the like of the coil wires are important. For example, voltages applied to the coil wires stands for such different voltages as that equivalent to a line voltage, a voltage to ground, and an inter-turn voltage. For such voltage values and frequencies, theoretical values obtained in advance from the actual machine or experimentally measured values such as ones obtained by multiplying safety factors may be used.

In the present embodiment having such a configuration, the conductive application-side permeable member 27 and the ground-side permeable member 37 both extending flat are opposed to each other with the test piece 10 therebetween. A uniform electric field thus occurs in the area of the test piece 10 sandwiched between the application-side permeable member 27 and the ground-side permeable member 37 except at the ends.

The reason is that while, for example, the aqueous solutions have a conductivity of approximately 1 S/m to 10 S/m, metal has a conductivity of the order of $10^7$ S/m, and potential distributions inside the application-side permeable member 27 and inside the ground-side permeable member 37 are both considered to be uniform. As a result, potential differences between the electrode holes 11 and the second surface 10b on the back side also become uniform.

Such application of the uniform electric field to the electrode holes can improve the accuracy of the reproducing test of a water tree.

Figure 4:
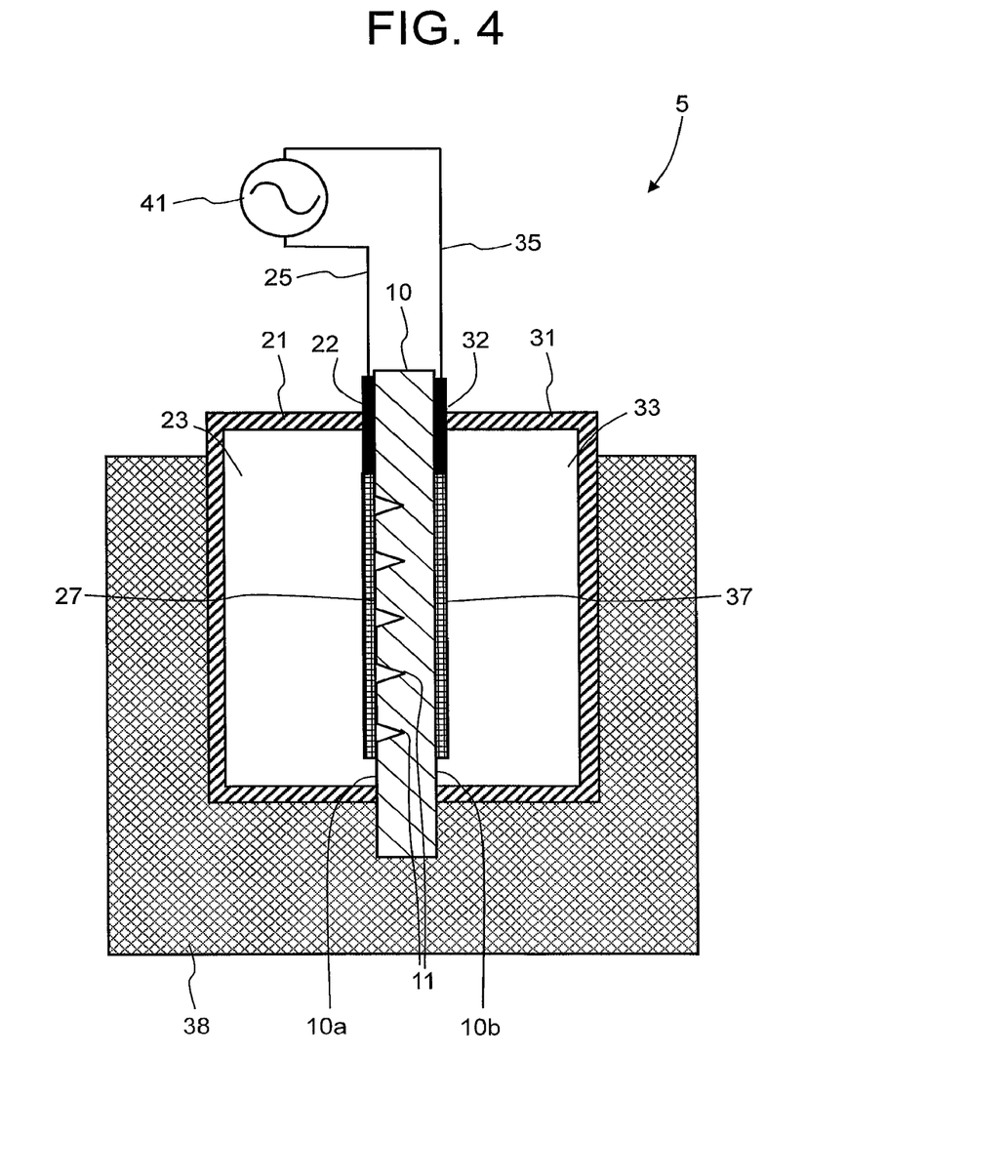
FIG. 4 is a sectional elevational view showing a configuration of a modification of the water tree testing apparatus.

The embodiment of the present invention has been described above. The embodiment has been presented by way of example and is not intended to limit the scope of the invention. For example, in the embodiment, the electrode on the side where the electrode holes 11 are formed is described to be the application-side electrode 22, and the electrode on the opposite side is described to be the ground-side electrode 32. However, this is not restrictive. The electrode on the side where the electrode holes 11 are formed may be a ground-side electrode and the electrode on the opposite side may be an application-side electrode as long as a potential difference is generated across the test piece 10 of candidate insulation material. In modifications, to examine a voltage polarity effect and the like, a voltage of positive polarity may be applied to the application-side electrode 22 on the side where the electrode holes 11 are formed and a voltage of negative polarity may be applied to the ground-side electrode 32 on the opposite side, and vice versa. As shown in FIG. 4, a conductive wire 25 from the application-side electrode 22 and a conductive wire 35 from the ground-side electrode 32 may be connected to an alternating-current power supply 41 so that an alternating-current voltage is applied between the application-side electrode 22 and the ground-side electrode 32.

In the exemplary embodiment, the application side of the alternating-current voltage is described to be connected to the conductive wire 24, the application-side electrode 22, and the application-side permeable member 27, and the ground side is described to be connected to the conductive wire 34, the ground-side electrode 32, and the ground-side permeable member 37. However, the application-side electrode 22 and the ground-side electrode 32 both may be omitted. More specifically, the conductive wire 24 may be directly connected to the application-side permeable member 27, and the conductive wire 34 may be directly connected to the ground-side permeable member 37.

Embodiments may be carried out in various other forms. Various omissions, substitutions, and modifications may be made without departing from the gist of the invention.

The embodiments and modifications thereof are included in the scope and gist of the invention, and included in the inventions described in the scope of claims and the range of equivalency thereof.

EXPLANATION OF REFERENCE SYMBOLS

5: testing apparatus, 10: test piece, 10a: first surface, 10b: second surface, 11: electrode holes (recesses), 21: application-side water tank, 22: application-side electrode, 23: application-side aqueous solution, 24, 25: conductive wire, 27: application-side permeable member, 31: ground-side water tank, 32: ground-side electrode, 33: ground-side aqueous solution, 34, 35: conductive wire, 37: ground-side permeable member, 38: insulator, 40, 41: alternating-current power supply, 50: rotating electrical machine, 51: stator, 52: rotor, 53: insulation member

The invention claimed is:

1. A water tree testing apparatus to reproduce a water tree phenomenon for a water tree resistance evaluation of a candidate insulation material by using a flat test piece of the candidate material, the test piece having a first surface in which a plurality of electrode holes are formed, the electrode holes being formed to decrease in cross section as approaching a bottom perpendicularly to the surface, the water tree testing apparatus comprising:
    a liquid-permeable conductive first permeable member that is attached to the first surface and extends along the first surface to cover the electrode holes;
    a liquid-permeable conductive second permeable member that is attached to a second surface that is opposite side from the first surface, and extends along the second surface as to face the first permeable member with the test piece therebetween;
    a first water tank that contains a first aqueous solution so that the first surface of the test piece including a range covered by the first permeable member is immersed in the first aqueous solution;
    a second water tank that contains a second aqueous solution so that the second surface of the test piece including a range covered by the second permeable member is immersed in the second aqueous solution;
    a first electrode whose one end is electrically connected to the first permeable member; and
    a second electrode whose one end is electrically connected to the second permeable member, wherein
    the first electrode and the second electrode are formed so that a voltage is applicable therebetween.

2. The water tree testing apparatus according to claim 1, wherein at least one of the first permeable member and the second permeable member is an electrically conductive porous metal plate.

3. The water tree testing apparatus according to claim 1, wherein at least one of the first permeable member and the second permeable member is a plate-shaped mesh of electrically conductive metal wires.

4. A water tree testing method for replicating a water tree phenomenon for a water tree resistance evaluation of a candidate insulation material by using a test piece of the insulation material, the water tree testing method comprising:
    a system setting step of setting a test system in such a state that a first permeable member is attached to a first surface of the test piece and the first surface is immersed in a first aqueous solution, and a second permeable member is attached to a second surface on a back side of the first surface and the second surface is immersed in a second aqueous solution, wherein
    the test piece is made of the candidate material, has a flat shape, and has a plurality of electrode holes formed in the first surface, and the electrode holes are formed to decrease in cross section as approaching a bottom perpendicularly to the surface;
    a voltage application step of grounding either the first electrode immersed in the first aqueous solution or the second electrode immersed in the second aqueous solution and applying an alternating-current voltage to the other after the system setting step;
    a measurement step of measuring an amount of development of a water tree in the test piece at predetermined time intervals after a start of the voltage application step; and
    a repeat step of determining whether a predetermined time of test time has elapsed after the measurement step, and if the predetermined time has elapsed, terminating the measurement step, and if the predetermined time has not elapsed, repeating the voltage application step and the measurement step.

* * * * *